United States Patent [19]

Grageda

[11] Patent Number: 4,637,034

[45] Date of Patent: Jan. 13, 1987

[54] COOLING PANEL FOR ELECTRIC ARC FURNACE

[75] Inventor: Ignacio J. Grageda, Puebla, Mexico

[73] Assignee: Hylsa, S.A., Monterrey, Mexico

[21] Appl. No.: 601,987

[22] Filed: Apr. 19, 1984

[51] Int. Cl.⁴ .............................................. E27D 1/12
[52] U.S. Cl. .................................................... 373/76
[58] Field of Search ...................... 373/73, 74, 75, 76; 266/190, 241, 280; 432/237, 238, 248

[56] References Cited

U.S. PATENT DOCUMENTS 4,207,060  6/1980  Zangs .
4,273,949  6/1981  Fischer et al. .

FOREIGN PATENT DOCUMENTS 2659827  4/1978  Fed. Rep. of Germany .
2825528  12/1979  Fed. Rep. of Germany .
2907511  9/1980  Fed. Rep. of Germany .
 908805  2/1982  U.S.S.R. .

OTHER PUBLICATIONS

Bleimann et al., An Update on Electric Arc Furance Melting with Water Cooled Side Panels and Up to 100% Sponge Iron, Iron and Steel Engineer, Aug. 1978, pp. 1-5.

K. S. Roberts & O. E. Prenn, Hot Spot Protection for UHP Electric Arc Furnaces Progress Report, I&SM, Apr. 1976, pp. 22-26.

Dr-Lng Ludger Zangs, Water-Cooled Linings for Direct Arc Melting Furnaces, Steel Times, Oct. 1978, pp. 912-916.

L. J. Voisinet, Worldwide Look at Electric Arc Furnace Performance, I&SM, Mar. 1975, pp. 44-49.

Primary Examiner—Roy N. Envall, Jr.
Attorney, Agent, or Firm—A. Thomas S. Safford

[57] ABSTRACT

A water cooling panel forms a part of or substitute for the wall of a metallurgical furnace, such as an electric arc furnace. The panel can be formed alternately as a tube type cooler formed of parallel pipes connected at its ends in headers, with the latter having internal baffles to define a serpentine path, or as a box type cooler formed of steel plates or sheet and having internal baffle plates defining a serpentine path for the cooling fluid. In either case, fluid orificies are provided to permit a minor amount of flow through the baffles or baffle plates where there is a direction change in the serpentine flow path. This serves to prevent stagnation, and prevent the problems of hot spots and steam bubbles where there is a change of direction in the cooling flow. Projections welded along the furnace-facing side of the panel permit the panel to be covered with a layer of refractory material or solidified slag.

24 Claims, 10 Drawing Figures

FIG. 9
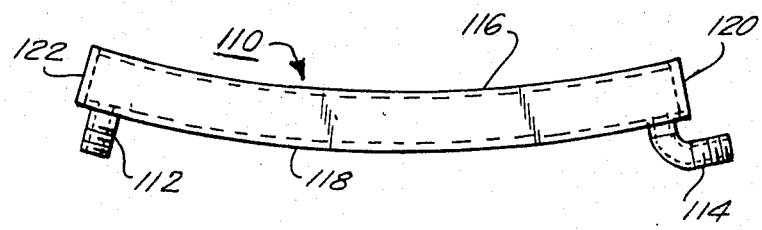
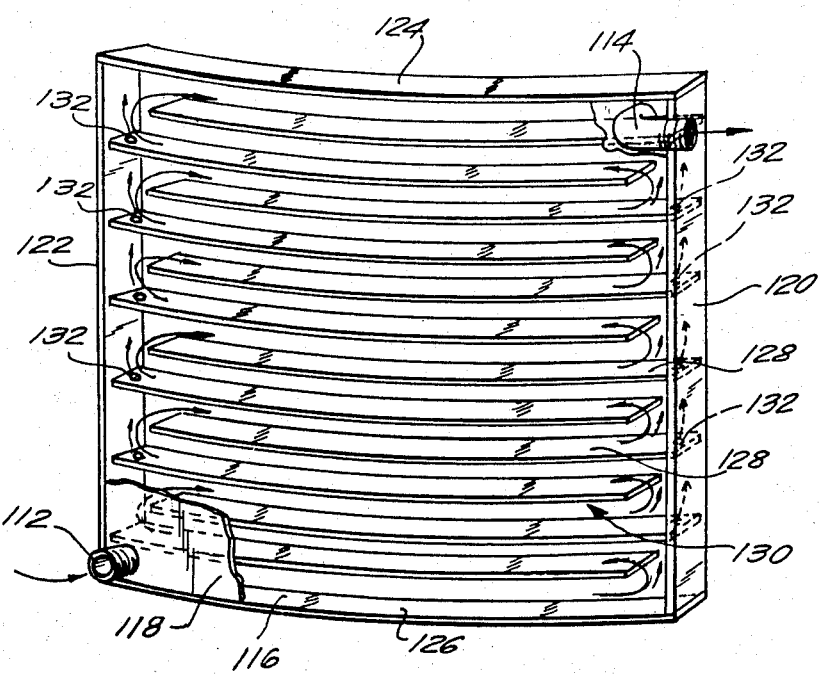
FIG. 10

COOLING PANEL FOR ELECTRIC ARC FURNACE

FIELD OF THE INVENTION

This invention relates to metallurgical processing, such as steelmaking; more particularly, this invention is directed to the construction of electric arc furnaces or similar high-temperature metallurgical furnaces. The invention is more specifically directed to cooling panels for the wall and roof of the electric arc furnace.

BRIEF DESCRIPTION OF THE PRIOR ART

A conventional electric direct-arc furnace, of the type employed in steelmaking, generally comprises a steel shell whose inner wall is lined with a refractory material. In normal use, the refractory material above the slag line generally has an expected durability of up to 350 heats, after which the furnace is relined with fresh refractory material.

Because of the high process costs involved in steelmaking, there has been a recent trend towards high power (HP) or ultra high power (UHP) operation. With ultra high power operation, the arc temperature is extremely high. While this has the beneficial effect of faster melting and higher productivity, the higher arc temperature can cause hot spots in the refractory wall. This in turn can lead to spalling, cracking, and other breakdown of the refractory material. Thus, the higher productivity achieved in high power or ultra high power operation is offset by the requirement to replace the refractory lining more often.

In order to reduce the refractory costs, and to lengthen the operative refractory life of electric arc furnaces, several approaches have been taken, either singly or in combination. These approaches include using higher quality refractory material, at least in the zone of hot spots near the electrodes; increasing the refractory thickness at the hot spots; using split furnace shells to reduce reline downtine; increasing the distance from the electrodes to the furnace sidewall by using tapered or barrel-shaped shells, and/or slanted masts and electrodes; employing automatic furnace control; and water-cooling the furnace walls, especially at the hot spot areas.

With regard to the last-mentioned approach, it has been discovered that the use of cooling panels above the slag line in arc furnaces would increase the refractory side wall life to at least twenty-five times that of normal refractory material, and that the use of cooling panels did not present a significant hazard to electric arc furnace operation. The water-cooled furnaces can employ cooling panels both for the shell walls and also for the furnace roof.

Generally, the entire cooling system is formed of a ring of cooling panels encircling the furnace interior above the slag line and an annular array of panels between the electrode apertures and the rim of the furnace roof.

The cooling panels are commonly of either of two types, namely, a box or plate cooler and a coil or tube cooler. The box cooler is generally formed by front and back plates defining an enclosed volume. Baffles may be employed within the enclosed volume to define a tortuous flow path between inlet and outlet tubes.

The coil or tube type cooler is generally formed of water-carrying tubes arranged in close juxtaposition. The tubes are generally connected, usually by means of a "U" or pipe bend at the ends of the successive pairs of tubes, to define a back-and-forth tortuous raster-like flow pattern through the tubes.

The tube-type cooler has the advantage of high mechanical strength, which permits it to absorb maximum mechanical impact loads, for example, during the times when steel scrap or sponge iron is charged into the furnace. The tubes of the tube-type cooler also permit more uniform cooling, thereby reducing thermal stresses.

Forced circulation of water or other cooling fluids through the cooling panels of either type is absolutely essential to achieve efficient and reliable cooling. In view of the fact that a great volume of water must flow quickly through the entire panel to absorb the enormous thermal load imposed by the electric arc, the melt, and the furnace gases, a tremendous pumping pressure is necessary. The tube-type cooler is superior in this regards, as it can withstand the high internal pressures much more readily than can the box-type cooler.

One problem encountered with either the box-type coolers or the tube-type coolers is the occurrence of steam pockets, particularly at "dead zones". These dead zones occur, for example, where there is an abrupt change in direction of flow. Film boiling can also occur in the vicinity of dead zones as there is no flow thereto to prevent it.

Such effects can lead to an abrupt loss of heat transfer capacity between the inner wall of the cooling panel and the cooling water. This, in turn, can cause a sharp rise in the temperature of the metal of the cooling panel itself, and can lead to "burn out" and possible fracturing of the material of the tube or plate.

Care taken in the design of the tube-type coolers and in dimensioning of the tubes and flow rate can help to combat this undesirable effect. However, it has not been heretofore possible to reduce the occurrence of "dead zones" by simple design considerations. Steam pockets and dead zones are still likely to occur at bends, especially at edges of the cooling panels, where there is a sharp change in direction of coolant flow.

OBJECTS AND SUMMARY OF THE INVENTION

Accordingly, it is an object of this invention to provide a cooling panel for an electric arc furnace which avoids the problems of the prior art.

More specifically, it is an object of this invention to provide a cooling panel which both permits the efficient removal of heat from the walls or the roof of an electric arc furnace, and substantially reduces or eliminates the occurrence of "dead zones".

It is yet another object of this invention to provide such a cooling panel in which at the location of directional changes of coolant flow in the panel there is a minor amount of flow provided, through a barrier or baffle between tubes so that the coolant is not permitted to stagnate and detrimental steam pockets and film steaming are not permitted to take place.

It is yet another object of this invention to provide a cooling panel for an electric arc furnace which is provided with suitable means for holding refractory material on its front surface.

According to an aspect of this invention, a cooling panel is provided for the wall or the roof of an electric arc furnace, and comprises a main cooling section through which a cooling fluid courses in a back-hand-forth, raster-like flow pattern from an inlet pipe to an outlet pipe. Baffle means are provided at the locations in the cooling panel where the stream of cooling fluid is to change directions. The baffle means each include at least one passage through the baffle means to permit a minor amount of the cooling fluid to flow through the baffle means. This prevents, or substantially reduces, the occurrences of "dead zones" in the vicinity of the sharp bends in the fluid stream.

In one embodiment, the cooling panels are arranged as tube or pipe coolers, having a plurality of lateral pipes arrayed in parallel and in close proximity to one another. A first header conduit connects the first ends of the lateral pipes and has respective openings communicating therewith; a second header conduit connects the second ends of the lateral pipes and has respective openings communicating therewith. Baffle means are disposed in the first and second header conduits between the respective ends of alternate adjacent ones of the lateral pipes such that the cooling fluid that enters the inlet pipe travels in a raster-like flow pattern back and forth from one lateral pipe to the next as it proceeds towards the outlet pipe. The baffle means each include at least one passage therein to permit a minor amount of the cooling fluid to flow through the baffle means so that occurrences of dead zones are substantially reduced in the vicinity of the first and second header conduits. Preferably, the minor flow is within about one percent to five percent of the total flow through the cooling panels. Also preferably, a plurality of pipe stubs are welded onto the lateral pipes and header conduits on the front or inwardly facing side of the panel. These pipe stubs serve for holding a layer of refractory material applied over the panel.

In another embodiment, the cooling panels are formed as box or plate coolers, and comprise a panel element having a front side facing the interior of the furnace and a rear side facing away from the furnace, with the sides defining therebetween an enclosed space. A plurality of fluid guide baffles each extend between the front side and the back side of the panel element from one edge towards the opposite edge of the enclosed space. These baffles each leave a principal opening at the opposite edge to permit a major amount of the cooling fluid to flow therethrough, with alternate fluid guide baffles having their respective principal openings at the first edge and the interleaved remaining fluid guide baffles having their respective principal openings at the other edge, such that the baffle means define a tortuous fluid pathway in the enclosed space, and the cooling fluid flows in a back-and-forth, raster-like flow pattern from the inlet pipe to the outlet pipe. The alternate and remaining fluid guide baffles each further include a passage or orifice disposed approximately at the second and first edges, respectively, to permit a minor amount of the cooling fluid to flow through the baffles to prevent occurrences of dead zones in the vicinity of the edges of the cooling panel element.

In this specification and in the accompanying drawings, there have been shown and described preferred embodiments of the present invention, and there have been suggested various alternatives and modifications thereof; but it is to be understood that these are not intended to be exhaustive and that many other changes and modifications can be made within the scope of the invention. These suggestions herein are selected and included for purposes of illustration in order that others skilled in the art will more fully understand the invention and the principles thereof and will thus be enabled to modify it in a variety of forms, each as may be best suited to the conditions of a particular use.

BRIEF DESCRIPTION OF THE DRAWINGS

FIGS. 9 and 10 are a top plan view and a schematic perspective view of a box-type cooling panel for an electric arc furnace also employing the principles of the present invention.

DETAILED DESCRIPTION OF THE PREFERRED EMBODIMENTS

Figure 1:
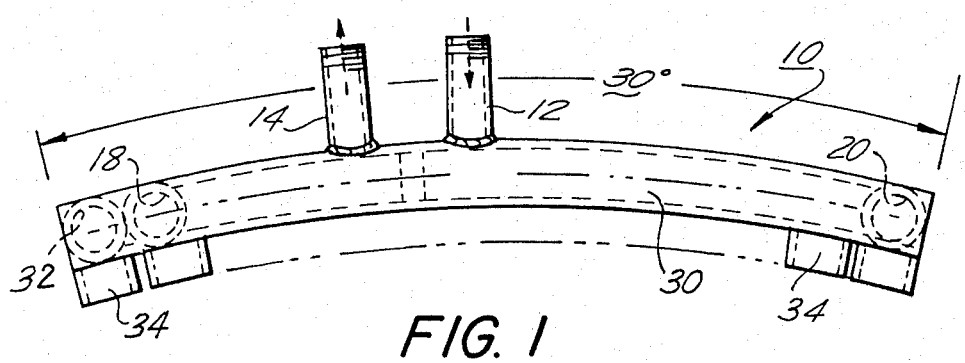
FIG. 1 is a top view of a wall cooling panel for an electric arc furnace according to one embodiment of this invention.
Figure 2:
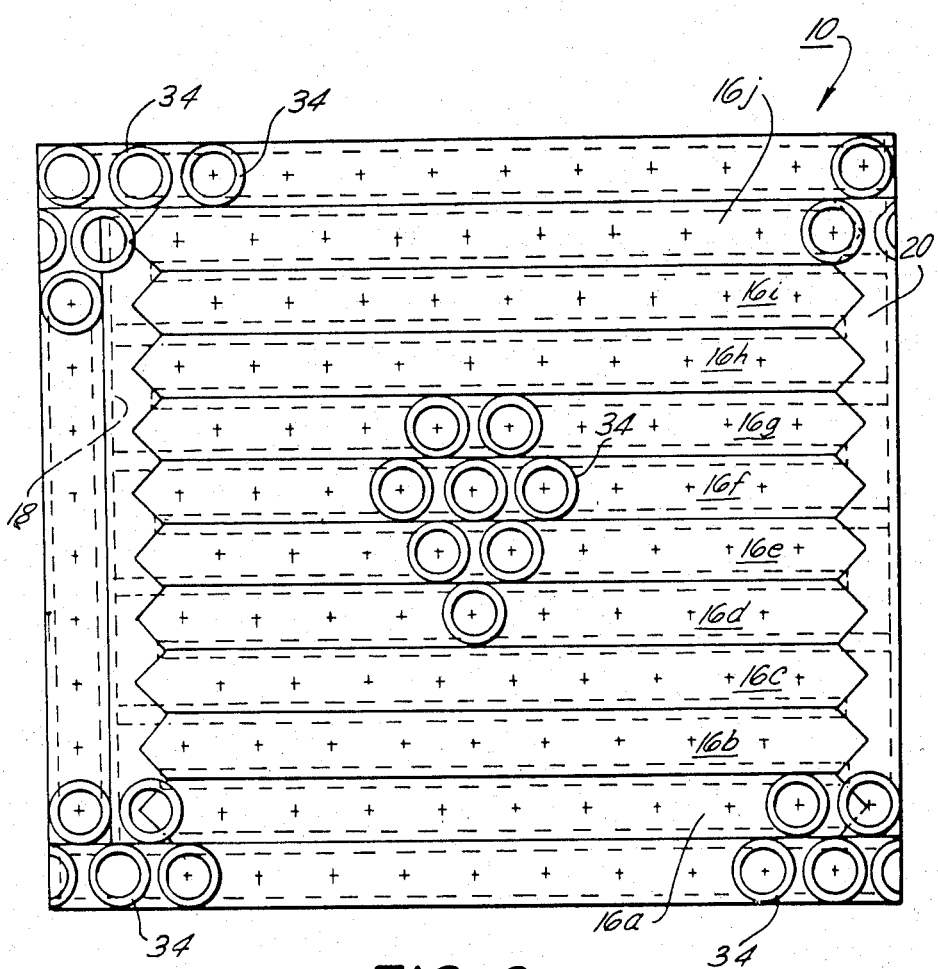
FIG. 2 is a front plan view of the wall cooling panel of FIG. 1.
Figure 3:
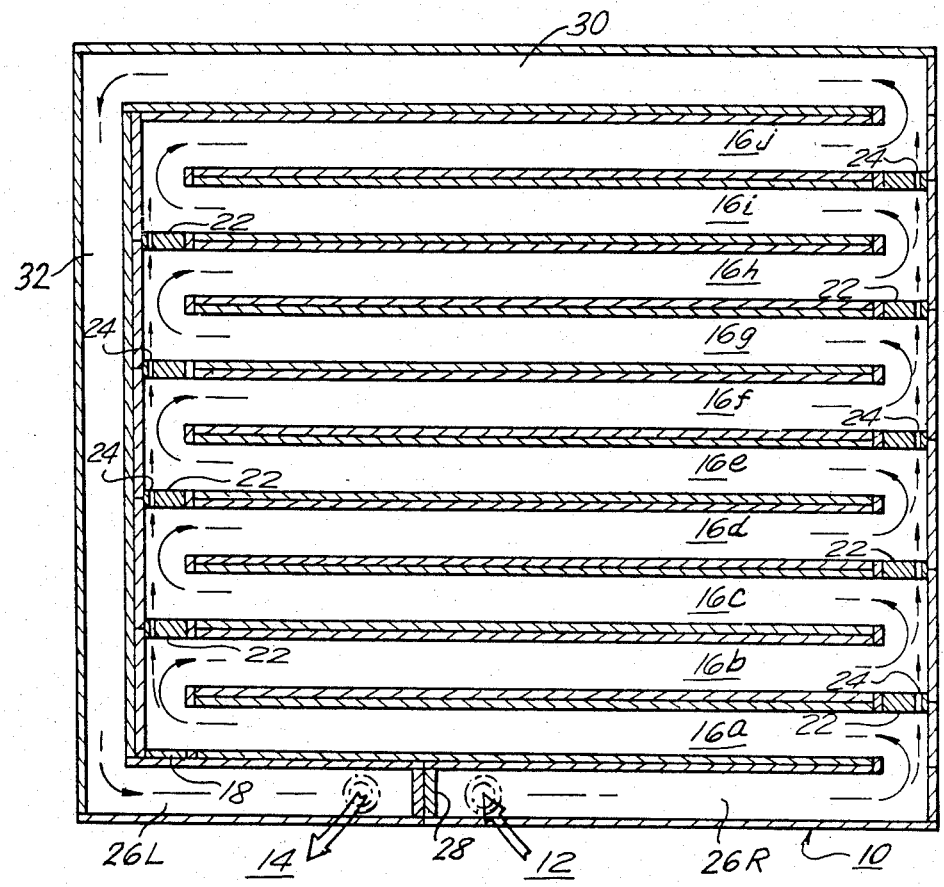
FIG. 3 is a sectional view of the wall cooling panel of FIG. 1.
Figure 7:
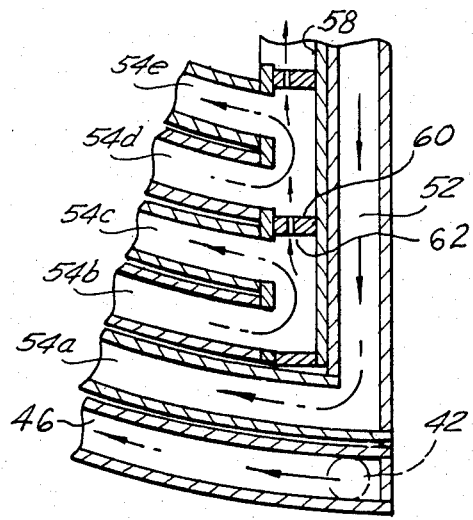
FIG. 7 is a detailed sectional view showing coolant flow through the roof cooling panel of FIG. 4.
Figure 4:
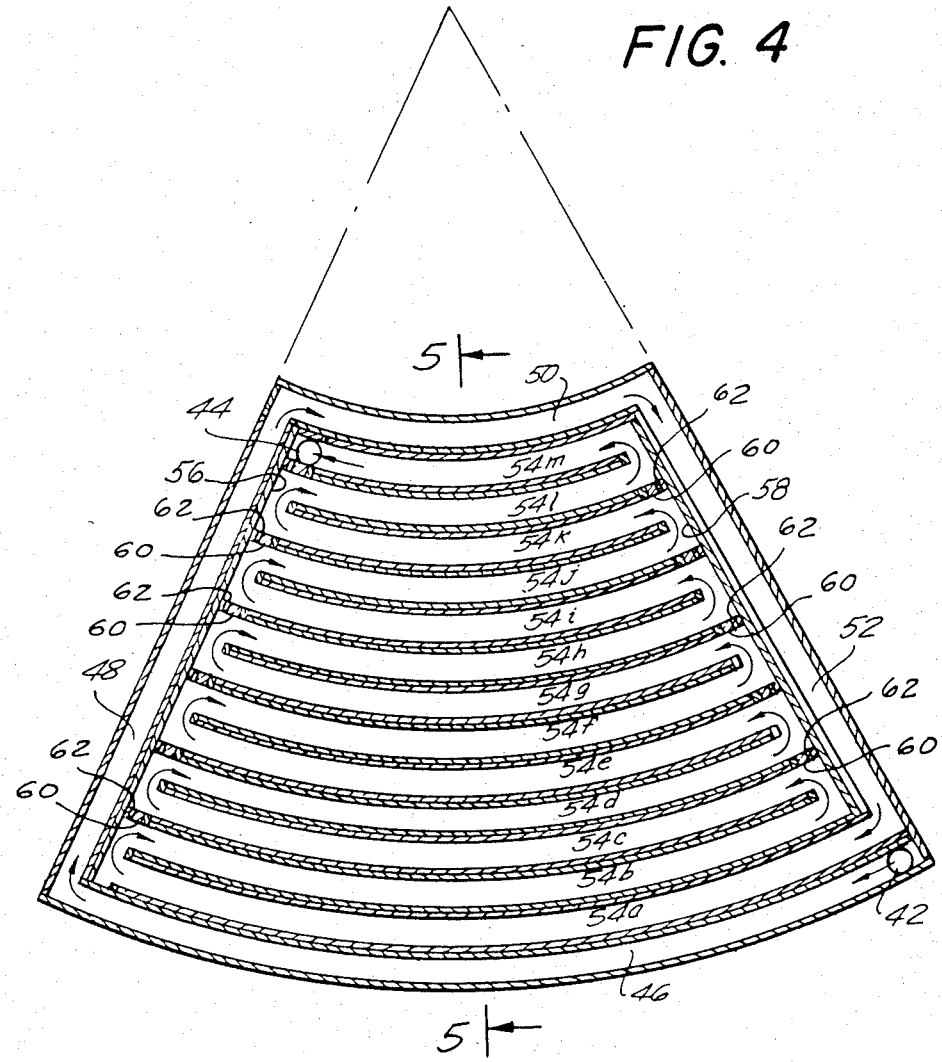
FIG. 4 is a sectional view of a roof cooling panel for an electric arc furnace according to this embodiment of the invention.

FIGS. 1-3 illustrate a preferred embodiment of a cooling panel for the wall of an electric arc furnace, the cooling panel incorporating the disclosed unique features embodying the present invention. In these FIGS. 1-3, a tube-type wall cooling panel 10 is comprised of a plurality of metal pipes welded together to form a more-or-less flat, but slightly arcuate array. As shown in FIG. 1, in this embodiment the panel forms a section of a cylinder, cutting an arc of substantially thirty degrees.

The cooling panel 10 has a water inlet tube 12 into which a cooling fluid, here preferably water, is supplied to the panel 10, at a water outlet tube 14 through which the cooling fluid is drained from the panel 10. A plurality of horizontal or lateral pipes 16a to 16j are joined side by side, for example by welding, and each has one end in fluid communication with a connecting header 18, at the left hand side of the drawings, and another end in fluid communication with a connecting header 20, shown at the right hand side of the drawings. These headers 18 and 20 (preferably pipes of the same diameter as the lateral pipes 16a16;) have openings joined to respective ends of the horizontal lateral pipes 16a to 16j.

A corresponding plurality of end baffles 22 are set into the headers 18, 20 between alternate ones of the ends of the pipes 16a to 16j. These end baffles 22 are staggered between the left and right connecting headers 18 and 20, to define a tortuous raster flow pattern through the lateral pipes 16a to 16j and the headers 18 and 20. As a result the cooling fluid entering the inlet tube 12 flows in a back-and-forth fluid path through the lateral pipes 16a to 16j on its way towards the outlet tube 14.

The end baffles 22 have passages or orifices 24 cut into them, preferably at the side nearest the outer edges of the baffles 22. The purpose of these passages 24 will be discussed later.

To complete the structure of this panel 10 there are illustrated a lowermost transverse pipe 26 having a baffle 28 therein, an uppermost transverse pipe 30 and a descending pipe 32. The baffle 28 divides the transverse pipe 26 into a portion 26L in direct fluid communication with the outlet tube 14 and another portion 26R in the direct fluid communication with the inlet tube 12. The portion 26R is further in direct fluid communication with the first of the lateral pipes 16a. The uppermost transverse pipe 30 is in fluid communication with the last of these lateral pipes 16j, and the descending pipe 32 connects the uppermost transverse pipe 30 with the first portion 26L of the lowermost transverse pipe 26.

As shown schematically in FIGS. 1 and 2, a plurality of pipe stubs 34 are butt-welded against the concave, or front side of the cooling panel 10. These pipe stubs 34 are illustratively shown only in the corners and center of the panel to eliminate unnecessary drawing clutter. However, in practice, these pipe stubs 34 would be evenly distributed over the entire front surface of the panel 10. That is, the pipes stubs 34 are welded at regular intervals to each of the elements 16a to 16j, 18, 20, 26, 30 and 32.

Prior to charging the electric arc furnace, these pipe stubs 34 serve to hold a gunning compound or other refractory material over the entire front surface of the panel. During the melt, and after pouring, these pipe stubs 34 collect slag and hold the solidified slag. These pipe stubs 34 also serve to improve the heat transfer characteristic of the panel 10 by serving as conductive fins. While pipe stubs 34 are employed in this embodiment, and provide optimum benefits, other projecting members could also be employed for a similar effect.

The passages or orifices 24 serve to combat the problem of hot spots and steam bubbles which would otherwise occur in the zones out of the main flow path of the cooling fluid, especially in the areas where the baffles 22 change the direction of the cooling fluid. These passages 24 permit a minor amount of the fluid to flow across the baffle, so that the fluid at bends in the tortuous fluid path is continuously being changed. This prevents stagnation which would lead to steaming or film vaporization of the fluid, and ensures good thermal contact at all points between the cooling fluid and the metal of the cooling panel 10.

FIGS. 4, 5, 6, and 7 illustrate a typical roof cooling panel 40 suitable for use in the roof of an electric arc furnace. This panel 40 is generally trapezoidal in shape, with sides thereof converging at an angle of slightly less than sixty degrees, so that six of these roof panels 40 can be employed to ring an annular zone of the roof between a central electrode opening therein and the rim of the roff.

Each such roof cooling panel 40 has an inlet tube 42 and an outlet tube 44. A lowermost transverse pipe 46 extends from the inlet tube 42 to an ascender pipe 48, extending along one converging edge of the panel 40 to an uppermost transverse pipe 50, which in turn connects with a descender pipe 52 disposed at the other converging side of the panel 40. A plurality of curved lateral pipes 54a to 54m, formed generally as arcs of concentric circles of progressively shorter length, have left and right ends joined respectively to a left-hand header 56 and a right-hand header 58. A plurality of baffle plates 60 are each disposed in the headers 56 and 58 between alternate ends of the lateral pipes 54a to 54m to define a tortuous raster flow path, as illustrated by the arrows in FIGS. 4 and 7. The first of these lateral pipes 54a is connected to the descender 52, and the last 54m thereof is coupled to the outlet tube 44.

As with the baffles 22 in the wall panel 10 previously discussed, the baffle plates 60 in the roof panel 40 have small passages or orifices 62 cut therein. These permit a minor amount of flow of the cooling fluid to pass through the baffle plates 60 at the places where there is a shap change of direction in the fluid path. Preferably, this minor flow amounts to about one to five percent of the total flow.

Figure 5:
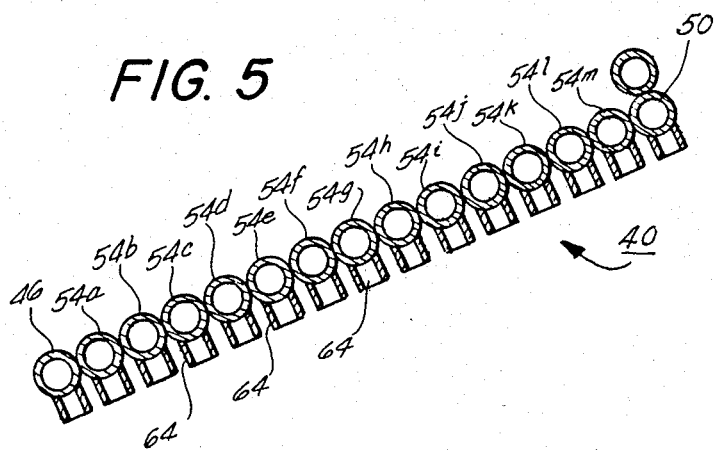
FIG. 5 is a side sectional view of the roof cooling panel of FIG. 4.
Figure 6:
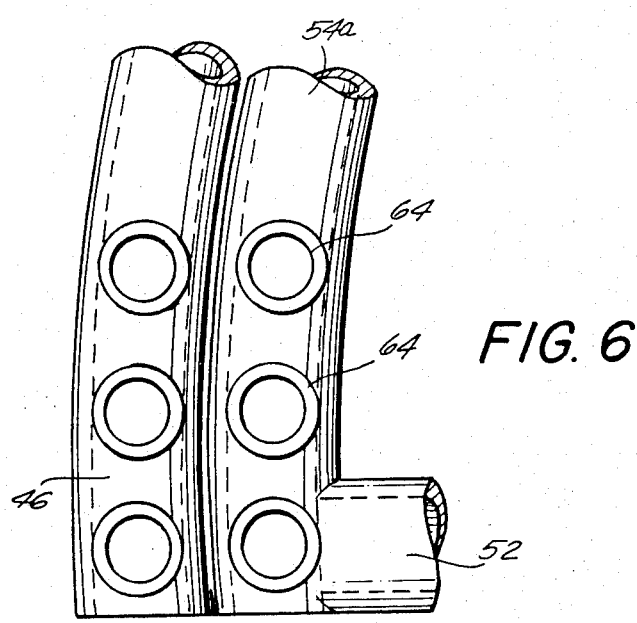
FIG. 6 is a detailed view of the roof cooling panel of FIGS. 4 and 5.

As illustrated in FIGS. 5 and 6, pipe stubs 64 are affixed, preferably by butt welding, at regular spaced intervals over the entire lower face of the panel 40. These pipe stubs 64 serve as projections to hold refractory material, such as gunning or solidified slag, in place over the panel 40.

Figure 8:
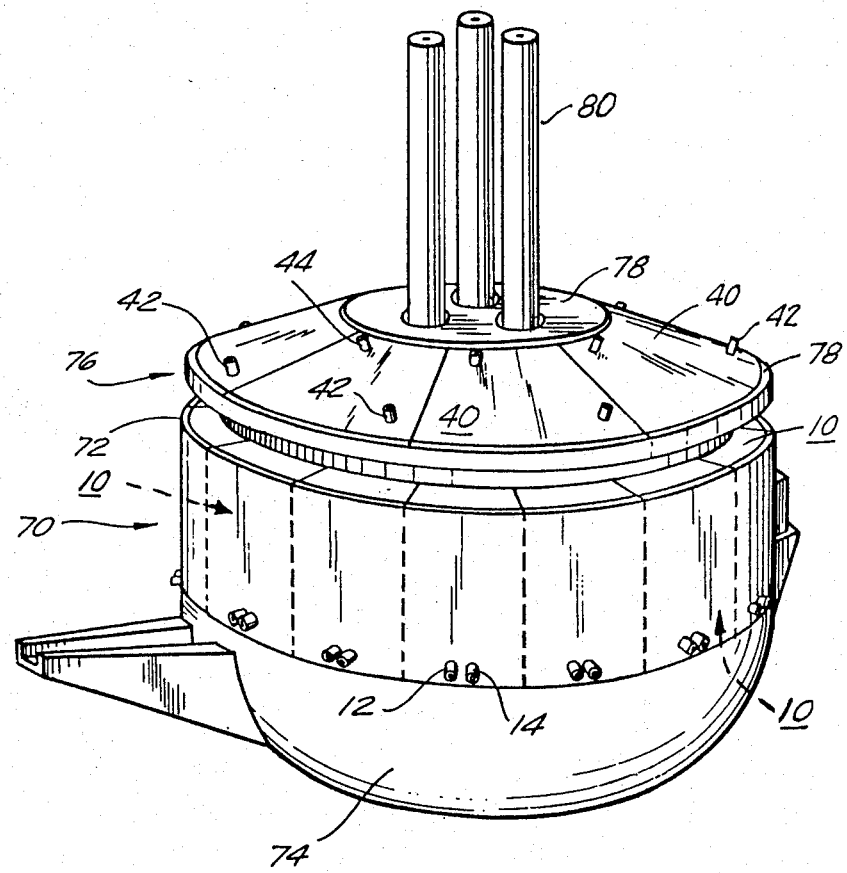
FIG. 8 is a perspective view of an electric arc furnace illustrating the employment of the wall cooling panels and the roof cooling panels of the first embodiment of this invention.

FIG. 8 illustrates in general terms the mode of employment of the panels 10 on an electric arc furnace 70. In some cases the furnace 70 has a steel shell 72 within which the panels 10 (shown in ghost lines) are affixed. Sometimes the panels 10 constitute the furnace wall making unnecessary a complete steel shell. The inlet tubes 12 and 14 extend through the shell 72 and are coupled to suitable flexible shielded conduits (not shown). A botttom 74 of the oven shell 72 forms a hearth section below the slag line of the furnace 70, and this hearth section is usually lined with fire brick or other refractory material. Normally, the bottom 74 is not exposed to the extreme heat of the electric arc, even in ultra high power operation. However, in the case of a single-electrode furnace, where a high current would be conducted through the furnace walls, the bottom 74 could also be protected with cooling panels.

A roof or cover 76 is formed of a roof shell 78 having a plurality (here, six) roof cooling panels 40 affixed thereto. These panels 40 are closely annexed to one another and form a ring or annulus between the rim of the roof shell 78 and an electrode opening at the center thereof. The inlet and outlet conduits 42, 44 of these panels are also connected to suitable flexible shielded fluid conduit (not shown).

Also illustrated are a plurality of vertically movable electrodes 80 for forming the arc of the electric arc furnace.

Preferably, the panels 10 and 40 are coupled through their respective flexible conduits to a suitable heat exchanger, so that the cooling fluid is maintained below a preferred temperature, such as 140° F. (60° C.).

FIGS. 9 and 10 illustrate another embodiment of this invention. In these figures, a "box" cooling panel 110 is formed of a front plate 116 and a rear plate 118, respectively disposed towards the furnace melt and towards the furnace shell. These plates 116 and 118, together with a left edge plate 120, a right edge plate 122, a top plate 124 and a bottom plate 126 define an enclosed space to which fluid is fed through an inlet tube 112 and from which the fluid is drained through an outlet tube 114.

A plurality of baffle members 128 extend between the front and rear plates 116, 118 and are alternately joined to the edge plates 120, 122, thereby leaving main flow passages at the other edge plates 122, 120, respectively. Thus, the baffle members 128 define a tortuous raster-like flow path 130 in which the fluid flows back and forth as it moves on its way from the inlet tube 112 towards the outlet tube 114.

Each of the baffle members 128 has one or more orifices 132 cut therethrough at the side that is joined to the respective left or right edge plate 120 or 122. Thus, while there is a major flow of the cooling fluid through the tortuous path 130, there is also a minor flow through the orifices 132, preferably amounting to one to five percent of the total flow. This minor flow prevents the problems of hot spots and steam bubbles at the locations where the baffle members change the direction of the main flow of the cooling fluid.

Terms of orientation, such as top, bottom, front, back, left, and right are used in the above description of the disclosed embodiments to facilitate understanding of the description thereof. However, the present invention is not limited to structure oriented in the fashion described above. For example, the principles of this invention could be employed as well where the fluid flow path changes alternately from upwards to downwards, as it is in the described embodiments where the serpentine flow alternately goes left and right.

While the principles of this invention have been embodied in certain detailed embodiments, it would be clear to those skilled in the art that many modifications and variations thereof are possible, without departing from the scope and spirit of this invention, which is to be defined by the appended claims.

What is claimed is:

1. Cooling panel for a furnace used in a metallurgical process, the panel comprising inlet means for supplying a cooling liquid; outlet means for withdrawing said cooling liquid; and enclosure means for coupling said inlet means to said outlet means for defining a tortuous liquid flow path which causes said cooling liquid to flow past essentially all portions of the interior face of said panel by passing seriatim through an array of side-by-side passages underlying said interior face, said tortuous flow path having a number of abrupt changes in direction and a shape resulting in potential dead zones at said abrupt changes in direction relative to the main flow through said path, and means for permitting a minor amount of said cooling liquid to flow along alternative liquid paths each into a respective dead zone from an adjacent passage such that at least in the central portion of said panel each successive occurrence of said dead zones are sufficiently reduced to prevent hot spots capable of causing burn out.

2. A cooling panel according to claim 1, wherein said tortuous flow path is defined by a plurality of horizontal baffles each having a free end opposingly offset from the free ends of adjacent baffles, and said means for permitting a minor amount of liquid flow includes passages through the respective closed ends of said baffles.

3. A cooling panel according to claim 1, wherein said minor amount of liquid flow is from about one percent to about five percent of the total flow of said cooling liquid, the liquid is water, and the alternative pathways are positioned to prevent formation of steam in the dead zones.

4. Cooling panel for a metallurgical furnace, comprising a plurality of lateral pipes arrayed in a substantially parallel file and in close proximity to one another each having first and second ends; a first header conduit connecting the first ends of said lateral pipes and having respective openings communicating therewith; a second header conduit connecting the second ends of said lateral pipes and having respective openings communicating therewith; inlet means for feeding a cooling liquid into said panel; outlet means for withdrawing the cooling liquid from said panel; and baffle means disposed in said first and said second header conduits between the respective ends of alternate adjacent ones of said lateral pipes such that the cooling liquid that enters said inlet means travels in a back-and-forth progressive flow pattern from one lateral pipe to the next as it proceeds towards said outlet means; wherein said baffle means each include at least one opening therein to permit a minor amount of said cooling liquid to flow through said baffle means such that occurrences of dead zones are substantially eliminated in the vicinity of said first and second header conduits.

5. Cooling panel for the wall of a metallurgical furnace according to claim 1, wherein said lateral pipes are curved such that the panel, viewed from above, defines an arc, and a plurality of said panels placed in proximity on the wall of the furnace form a circle.

6. Cooling panel for a metallurgical furnace according to claim 4, wherein said furance is an electric arc furnace.

7. Cooling panel for an electric arc furnace according to claim 6, wherein said lateral pipes and said header conduits have welded thereto, on the side of the panel facing radially inwards when in place in the furnace, a plurality of projections for holding refractory material applied over said panel.

8. Cooling panel for an electric arc furnace recording to claim 7, wherein said projections are welded at regular intervals over substantially the entire inwardly facing side of the panel.

9. Cooling panel for the wall of a metallurgical furnace according to claim 4, wherein said panel includes a bottom transverse pipe having first and second ends and disposed at a lower edge of said panel and coupled at its first end to said first header conduit at its lower end; conduit means extends from an uppermost one of said lateral pipes to the second end of said bottom transverse pipe; and a baffle disposed in said bottom transverse pipe obstructs flow of liquid therethrough; said inlet means feeds said cooling liquid into said bottom transverse pipe on one side of said baffle and said outlet means drains said liquid from said bottom transverse pipe at the other side of said baffle.

10. Cooling panel for the wall of a metallurgical furnace according to claim 9, wherein said inlet means includes an inlet tube disposed on the side of said baffle towards said first end of said bottom lateral pipe and said outlet means includes an outlet tube disposed on the side of said baffle towards said second end of said bottom lateral pipe.

11. Cooling panel for the wall of a metallurgical furnace according to claim 10, wherein said inlet and outlet tubes extend in the direction radially outwards with respect to said furnace.

12. Cooling panel for the roof of an electric are furnace according to claim 4, wherein the plurality of lateral pipes are arranged as corresponding arcs of concentric circles and in close proximity to one another.

13. Cooling panel for the roof of an electric arc furnace according to claim 12, wherein said lateral pipes are of progressively greater length from a radially inward position to a radially outward position with respect to said roof, so that said panel is generally trapezoidal.

14. Cooling panel for the roof of an electric arc furnace according to claim 13, wherein said lateral pipes said header conduits have welded thereto, on the downward-facing side of said panel, a plurality of projections for holding refractory material applied onto said panel.

15. Cooling panel for the roof of an electric arc furnace according to claim 14, wherein said projections are welded at regular intervals over substantially the entire downward-facing side of said panel.

16. Cooling panel for the roof of an electric arc furnace according to claim 12, wherein said panel includes bottom transverse pipe extending along a lower edge of said panel, an ascender conduit connected at one end to an end of said bottom lateral pipe and extending parallel to said first header conduit, a descender conduit extending parallel to said second header conduit and coupled at one end to the lateral pipe next adjacent said bottom transverse pipe, and a top transverse conduit connecting the other ends of said ascender and descender conduits; and wherein said inlet means is coupled to the other end of said bottom transverse pipe and said inlet conduit is coupled to the lateral pipe next adjacent said top transverse pipe.

17. Cooling panel for the roof of an electric arc furnace according to claim 16, wherein said inlet means includes an inlet tube and said outlet means includes an outlet tube, said inlet tube and said outlet tube extending upwards away from said electric arc furnace.

18. Electric are furnace having liquid cooled roof and walls, comprising cooling panels according to claim 4, a first shell defining wall and bottom of the furnace, a refractory lining in the bottom of the furnace, and a plurality of said cooling wall panels disposed in the wall of said shell above said bottom; and a roof shell dimensioned to fit over the top of said first shell and having electrode passages therein, and a plurality of said cooling panels disposed around said roof shell.

19. Electric arc furnace according to claim 18, wherein said baffle means each include a baffle plate having a bore therethrough.

20. Electric arc furnace according to claim 18, wherein said minor amount of flow is between about one percent and five percent of the total flow of fluid through said panel.

21. Cooling panel for a metallurgical furnace comprising a panel element having a front side facing the interior of said furnace and a rear side facing away from said furnace, the sides defining therebetween an enclosed space having first and second opposite edges; inlet means for supplying a cooling liquid into said enclosed space; outlet means for withdrawing said cooling liquid from said enclosed space; and a plurality of liquid guide baffle means each extending between said front side and back side from one said edge towards the opposite edge of the enclosed space and leaving a principal opening at said opposite edge to permit a major amount of said cooling liquid to flow therethrough, with alternate ones of said liquid guide baffle means having their respective principal openings at said first edge and the interleaved remaining ones of said liquid guide baffle means having their respective principal openings at said second edge such that said baffle means define a tortuous liquid pathway in said enclosed space and said cooling liquid flows in a back-and-forth raster-like progressive flow pattern from said inlet means to said outlet means; said alternate and remaining liquid guide baffle means each further include a passage therethrough approximately at said second and first edges, respectively, to permit a minor amount of said cooling liquid to flow through said baffle means such that the dead zones occurring in the vicinity of said respective first and second edges are substantially reduced.

22. Cooling panel for a metallurgical furnace according to claim 21, wherein said passage is dimensioned such that said minor flow is about 1% to 5% of the total flow through said tortuous pathway.

23. Cooling panel for a metallurgical furnace according to claim 22, wherein said panel is a box cooler including a front plate and a rear plate forming said front and rear sides, respectively.

24. Cooling panel for a metallurgical furnace according to claim 23, further comprising a plurality of protruding members affixed onto the exterior of said front side for holding refractory material applied over said panel.

* * * * *